United States Patent
Kamath et al.

(10) Patent No.: US 9,198,494 B2
(45) Date of Patent: Dec. 1, 2015

(54) METHOD AND CHEMICAL COMPOSITIONS FOR RESHAPING HAIR

(71) Applicants: Yashavanth Kamath, Princeton, NJ (US); Mort Westman, Oak Brook, IL (US)

(72) Inventors: Yashavanth Kamath, Princeton, NJ (US); Mort Westman, Oak Brook, IL (US)

( * ) Notice: Subject to any disclaimer, the term of this patent is extended or adjusted under 35 U.S.C. 154(b) by 0 days.

(21) Appl. No.: 14/492,409

(22) Filed: Sep. 22, 2014

(65) Prior Publication Data
US 2015/0020838 A1  Jan. 22, 2015

Related U.S. Application Data

(63) Continuation of application No. 13/103,097, filed on May 8, 2011, now abandoned.

(51) Int. Cl.
| | |
|---|---|
| *A61K 8/92* | (2006.01) |
| *A61Q 5/04* | (2006.01) |
| *A45D 7/06* | (2006.01) |
| *A45D 2/00* | (2006.01) |
| *A61K 8/19* | (2006.01) |

(52) U.S. Cl.
CPC *A45D 7/06* (2013.01); *A45D 2/001* (2013.01); *A61K 8/19* (2013.01); *A61K 8/922* (2013.01); *A61Q 5/04* (2013.01); *A61K 2800/882* (2013.01); *A61K 2800/884* (2013.01)

(58) Field of Classification Search
CPC ... A45D 2/001; A45D 7/06; A61K 2800/882; A61K 8/19; A61K 8/922
See application file for complete search history.

(56) References Cited

U.S. PATENT DOCUMENTS

| 5,609,859 | A * | 3/1997 | Cowsar | 424/70.4 |
| 7,297,673 | B2 * | 11/2007 | Collin et al. | 510/475 |
| 2003/0185785 | A1 * | 10/2003 | Moyal | 424/74 |
| 2009/0280079 | A1 * | 11/2009 | Gray et al. | 424/64 |
| 2010/0092416 | A1 * | 4/2010 | Luengo et al. | 424/70.6 |

* cited by examiner

*Primary Examiner* — Anna Falkowitz
(74) *Attorney, Agent, or Firm* — TechCoastLaw (57) ABSTRACT

The current invention comprises methods and compositions for straightening hair. Using embodiments of the current invention, curly hair can be effectively and safely straightened by a method that is milder and less damaging than the current art and does not employ ingredients such as formaldehyde and glutaraldehyde that are considered noxious and raise significant toxicological concerns. In one or more embodiments of the invention, a low concentration of sodium hydroxide (~0.5-0.6%) is applied prior to the application of an oil (preferably a vegetable oil), followed by treatment with a flat iron, or similar, heated to ~180-200° C. In one or more alternative embodiments of the invention, the sodium hydroxide and oil-containing compositions are combined and applied to the hair in a single step. The improvements extended by this invention beyond the current art include: reduced damage to hair; reduced potential for damage to the skin and eyes; elimination of noxious chemicals; avoidance of chemical systems that are banned in a number of countries; greater resistance to reversion; longer lasting results; and as a consequence of these considerations, potential for home (non-professional) usage.

18 Claims, 2 Drawing Sheets

METHOD AND CHEMICAL COMPOSITIONS FOR RESHAPING HAIR

CROSS REFERENCE TO RELATED PATENT APPLICATIONS

This patent application is a continuation of U.S. patent application Ser. No. 13/103,097 filed on May 8, 2011 which is incorporated by reference in its entirety herein.

FIELD OF THE INVENTION

The present invention relates to the field of hair care, and, in particular, to a method and chemical compositions for reshaping hair.

BACKGROUND OF THE INVENTION

Human hair naturally grows in a number of shapes. For example, some persons have naturally straight hair, others have naturally curly hair. For fashion, appearance, manageability, or other reasons, persons often desire to change the shape of their hair from curly to various degrees of straight, or vice versa.

The shape of human hair depends on the chemical composition and molecular arrangement of its keratin protein, primarily as it appears in the cells of the cortex. Keratin protein in these cortical cells is present in two different forms: as alpha helices stabilized by intramolecular hydrogen bonds to form stiff rods known as intermediate filaments, and as an amorphous mass in which the intermediate filaments are embedded. Importantly, disulfide bonds serve both to make this amorphous matrix rigid and to connect it to the intermediate filaments. The overall configuration of the hair fiber, curly or otherwise, depends on these structures and the cross-sectional shape of the follicle from which the fiber emerges. Thus, in hair, keratin is a structural protein that is characteristically crosslinked by disulfide bonds which are greatly responsible for its strength and configuration.

During the process known as permanent waving, hair is reacted with a reducing agent such as ammonium thioglycolate thereby breaking a significant number of its disulfide bonds and converting them into the corresponding thiols. Then the hair is forced into a revised configuration by wrapping it around a cylindrical mandrel (curling or waving rod) with some degree of tension, and the thiol groups are reacted with an oxidizing agent such as hydrogen peroxide to form new disulfide bonds which stabilize the revised configuration. In the absence of further chemical treatment, when removed from the mandrel, the hair retains its new, spring-like, curled shape. Correspondingly, this process is known as permanent waving. Although termed permanent, in the presence of water, and/or oxygen, and/or trace minerals and/or sunlight, hair treated by this process may slowly revert to its natural shape through these same reactions, albeit at a greatly decreased rate. Conversely, curly hair can be straightened by this same chemical process by maintaining the hair in a straightened configuration while the disulfide bonds are reformed through oxidation. Similar to hair curled by this process, thus straightened hair tends to revert to its earlier configuration through reverse reactions (disulfide cleavage and re-formation) occurring slowly over a period of time.

The configuration of hair that has been straightened or curled can, however, be stabilized to some degree by subjecting it to temperatures that are adequately high to cause its proteins to crosslink through its carboxyl, hydroxyl and amino groups. The resultant covalent crosslinks are more resistant to cleavage and therefore, more stable than the more chemically reactive disulfide bonds. Relatively high temperatures (150° C. and above) are required to create these crosslinks since most such reactions require dehydration. Given that a significant portion of the rods upon which hair is wound during permanent waving are in close proximity to the scalp it would be dangerous to apply such high temperatures to stabilize the resultant curls. In contrast, this can be achieved during straightening by stretching hair in a direction away from the scalp between heated flat plates in appliances known by such names as flat irons and hair straighteners.

The bulk density and curliness of an individual's hair ranges from thin and straight to dense and curly. The first significant attempts at straightening very dense and curly hair used "hot combs." During this process the curly hair was softened by the considerable heat of the hot comb and, in effect, stretched to straightness. The high temperature employed caused some degree of protein crosslinking but also rendered the hair brittle and excessively damaged. Often greases, and/or waxes, and/or oils (e.g., lanolin, petrolatum, beeswax, mineral oil) were applied to lubricate hair during the process and to reduce damage during stretching as well as to provide a superficial degree of remedial smoothness and shine.

An improvement over the hot comb procedure was provided by the "lye" based systems containing sodium hydroxide as the active chemical. The more modern versions of these contain 2.0-2.5% (unless otherwise noted, all percentages cited herein reflect weight by weight (w/w) measures) sodium hydroxide in the form of a cream emulsion. The high concentration of alkali in such formulations swells and softens hair to a much greater degree than did the hot comb procedures. Consequently, it can be straightened by relatively gentle stretching at room temperature resulting in improved results and less damage to the hair as compared with the earlier hot comb procedure. Proper post-treatment neutralization of hair is important to recovery of its mechanical properties although most commercial acidic shampoos employed for this purpose are not adequately effective. While lye systems are effective in straightening hair, the alkali is irritating to the scalp and inflicts significant damage to hair, albeit without the level of embrittlement caused by heating appliances.

The straightening of very curly hair and its stabilization is known to be partly due to the formation of lanthionine crosslinks which are more resistant to cleavage than disulfide bonds. Desire to minimize the hazards, as well as the negative consumer opinion associated with the use of lye, led to the development of what has been termed the "no lye" systems based on calcium hydroxide and guanidine carbonate. This combination, which must be kept apart prior to use, forms guanidine hydroxide and works by the same mechanism as does sodium hydroxide. Because this combination generates alkali in situ, its main advantage as compared with sodium hydroxide based systems is that the concentration of alkali in the vicinity of the scalp and hair is much lower at any given time and thus less irritating and damaging, respectively.

Apart from individuals with very curly hair, individuals with a lesser degree of curl often desire to straighten their hair either driven by fashion or the desire for improved manageability. Given its lesser degree of curliness, such hair does not require the severe processes described above. The numerous products commercialized for this purpose tend to fall into one of the following two categories: Products that employ a reducing agent such as salts of thioglycolic acid or sodium bisulfite to reduce (cleave) the disulfide bonds, and then oxidize the hair in a new, straightened configuration (as in permanent wave technology); or products that straighten and cross link hair with the use of highly heated (190-230° C.) appliances (e.g., flat iron and hair straightener) with or without the use of cross linking chemicals (most notably formaldehyde and glutaraldehyde). While the latter category provides significantly longer lasting results it requires a far more tedious, lengthy and expensive process (which, typically, must be performed only by a professional); inflicts greater damage to hair; and the agents employed for crosslinking (notably formaldehyde) are noxious and raise toxicological concerns to the extent that they have been banned in a number of countries.

SUMMARY OF THE INVENTION

Using embodiments of the current invention, curly hair can be effectively and safely straightened by a method that is milder and less damaging than the current art and does not employ ingredients such as formaldehyde and glutaraldehyde that are considered noxious and raise significant toxicological concerns. In one or more embodiments of the invention, a low concentration of sodium hydroxide (~0.5-0.6%) is applied prior to the application of an oil (preferably a vegetable oil), followed by treatment with a flat iron, or similar, heated to ~180-200° C. In comparison, current straightening products containing sodium hydroxide products employ this ingredient in concentrations of 2.0-2.3% and those non-sodium hydroxide products that employ heat, employ temperatures in the range of 190-230° C. It should be noted that prior to the invention described herein, it was not feasible to employ substantial heat (e.g., that typically employed by a straightening iron) in conjunction with sodium hydroxide or no-lye (guanidine carbonate-calcium hydroxide) hair straightening formulas because, due to the high level of alkali contained in these products, this would result in extraordinary damage to the hair and pose substantially increased risk of injury to the skin and eyes. In one or more alternative embodiments of the invention, the sodium hydroxide and oil-containing compositions are combined and applied to the hair in a single step. The improvements extended by this invention beyond the current art include: reduced damage to hair; reduced potential for damage to the skin and eyes; elimination of noxious chemicals; avoidance of chemical systems that are banned in a number of countries; greater resistance to reversion; longer lasting results; and as a consequence of these considerations, potential for home (non-professional) usage.

DETAILED DESCRIPTION OF THE PRESENT INVENTION

One or more embodiments of the present invention employ oils that are used in the prior art or are similar to those used in the prior art, but instead of solely serving an adjunct purpose (e.g., conditioning, lubricating, basis for marketing claims to enhance consumer appeal/salability) as in the prior art, they are employed as required reactants in the chemical straightening process and thereby serve as functional ingredients as well as integral components of the invention.

In one example use of an embodiment of the present invention, tresses of human hair were treated for approximately 15 minutes under ambient conditions with a low concentration of aqueous sodium hydroxide (~0.6%). Selection of a low concentration of sodium hydroxide and a relatively brief time of treatment, provided the high pH required to swell the hair yet caused negligible damage to the hair compared with the prior art and, in practice, would reduce risk to the skin and eyes. Subsequently, the tresses were pulled through the thumb and index finger with squeezing to remove excess solution (capillary liquid) and then combed for the same purpose. Without rinsing, the tresses were then treated for 20 min. with a solution of 8% soybean oil in a 5:1 alcohol:acetone mixture. Then the tresses were once again squeezed to remove water and combed through to remove excess solution; lightly blow dried (12-18" from tress) to remove solvents (this blow drying step is considered optional); and stretched to straightness between the blades of a flat iron at 180-200° C. After cooling, the tresses were wetted with cold water, shampooed, and rinsed with cold water before being air dried. Tresses were then immersed in an aqueous solution of shampoo maintained at 50-55° C. for 30 min. and allowed to air dry before evaluating straightening results. Shampooing immediately after completion of the straightening treatment was performed to determine the minimum straightening performance to be anticipated of an embodiment because such effectiveness is anticipated to increase with tress aging prior to shampooing. Delayed shampooing would allow residual chemicals to remain in contact with hair for a prolonged period of time and thus provide additional/more effective cross link formation. Shampooing at an exaggeratedly high temperature was performed as an accelerated test to predict the durability of the straightening imparted to hair after being subjected to the real life challenges of repeated shampooing and extended exposure to the environment.

Repetition of this study employing various greases, waxes and/or oils (greases, waxes and/or oils are hereafter referred to as oil or oils) repeatedly demonstrated that hair subjected to pretreatment with dilute sodium hydroxide retained its straightness to a far greater degree than had hair that was treated exactly in the same manner except for this step. The results of these studies are summarized in Table 1 below. These studies also revealed that hair treated with greases, waxes and/or oils subsequent to the sodium hydroxide treatment retained its straightness to a far greater degree than had hair that was treated exactly in the same manner except for this step. This suggests that the beneficial effect of embodiments of the current invention is due in part to the oil that has penetrated hair that was swollen as a result of being subjected to high pH and heat. Further, addition of the oil treatment step resulted in a degree of straightening that had hitherto required the use of a much higher concentration of sodium hydroxide. This is particularly important because sodium hydroxide is, in effect, a necessary evil in hair straightening formulations because in addition to providing functionality it is also damaging to hair, skin and eyes. Because the magnitude of both these beneficial and detrimental effects increases with sodium hydroxide concentration, the ability to achieve straightening with less sodium hydroxide reduces the potential for accompanying damage to hair, skin and eyes. Further, as described above, the effective use of lower concentrations of sodium hydroxide or other alkaline materials enables the use of substantial heat during the process.

The temperature employed when treating tresses with an electrical flat iron in one or more embodiments of the invention, approximately 180-200° C., is significantly lower than those reached by electrical flat irons, which can be heated as high as 232° C.

In one or more embodiments, any of a variety of oils, including, without limitation, coconut, olive, flax seed and soy bean oil may be used, although their performance may vary. It is believed that at high temperatures the oil undergoes hydrolysis and the resultant fatty acids react with the proteins of hair to form hydrophobic crosslinks. This stabilizes the protein structure and reduces the sensitivity of hair to water, thus making the straightened configuration more permanent.

Figure 1:
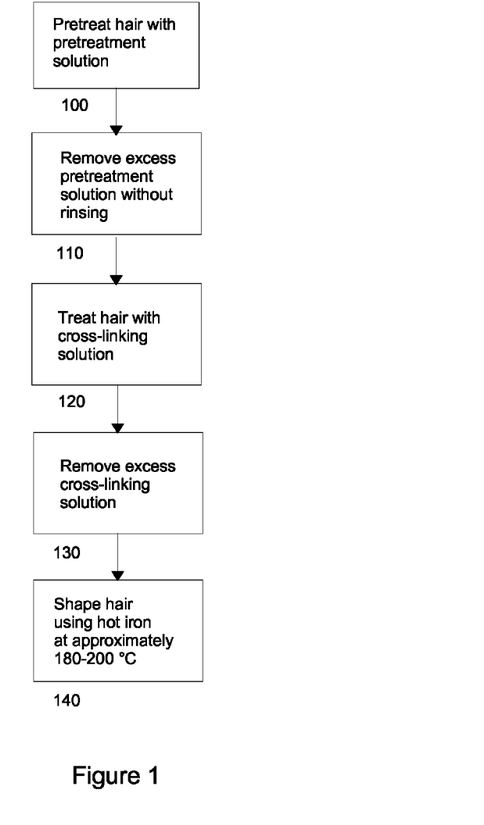
FIG. 1 is a flow chart illustrating the steps of a method used in one or more embodiments of the invention.
Figure 2:
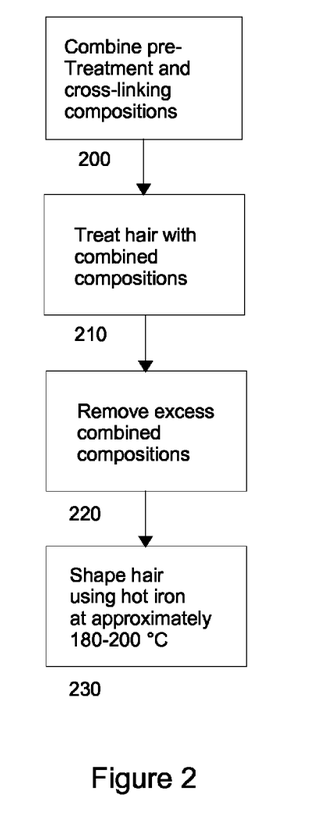
FIG. 2 is a flow chart illustrating the steps of a method used in one or more embodiments of the invention.

FIG. 1 shows a process used to reshape hair in one or more embodiments of the invention. At step 100, the hair is pretreated with a pretreatment solution, for example a solution containing a low concentration of sodium hydroxide (e.g., approximately 0.5%) for sufficient time to swell the hair (e.g., approximately 15-20 minutes). At step 110, excess sodium hydroxide solution is removed without rinsing, for example by squeezing, combing, or being partially dried by a towel. At step 120, the hair is treated with a cross-linking solution (e.g., an oil in solution, such as, for example 8% soybean oil in a 5:1 alcohol acetone mixture). In one or more embodiments, the cross-linking solution is maintained on the hair for approximately 20 minutes. At step 130, the excess cross-linking solution is removed, for example by squeezing, combing, or being partially dried by a towel. In one or more embodiments, the hair is lightly blow dried to remove remaining solvents. At step 140, the hair is shaped with tension using a hot iron (e.g., a flat iron) at a temperature of approximately 180-200° C.

The oil, fat, grease or wax component used in one or more embodiments of the invention can be of vegetable or mineral/petroleum origin (including chemical modifications and derivatives thereof) and can be employed neat or in a variety of forms including solution, emulsion and dispersion. For example, one of the embodiments employs vegetable seed oil bodies in the form of oleosomes (Hydresia™ by Botaneco)

Table 1 below lists experimental data derived from a number of embodiments of the process to reshape hair of the present invention. In Table 1, the first column identifies an Embodiment Number, the second column identifies the Pretreatment Solution used, the third column identifies the Cross-Linking Composition (X-Link) used, the fourth column contains Comments, and the fifth column contains a Rating of the relative effectiveness of that procedure. The following hair treatment procedure ("Hair Treatment Procedure") was employed to obtain the data in Table 1:

Hair Treatment Procedure:

Step 1: Soak tress of human hair (~2 g, 15-20 cm length) in excess of NaOH Solution for 15 min. (2 g hair: 30 ml solution).

Step 2: Squeeze excess NaOH Solution from tress by pulling between gloved thumb and index finger. Comb through tress for same purpose.

Step 3: Soak tress in excess Cross-Linking Composition (2 g tress: 30 ml Cross-Linking Composition) for 20 minutes.

Step 4: Squeeze excess Cross-Linking Composition from tress, comb and blow dry to remove any volatile solvents (e.g., ethanol, acetone) but leaving hair damp with water.

Step 5: Pull flat iron (set at 180-200° C.) through the tress with tension. Typical time is 1 minute.

Step 6: Immerse in "cold" tap water followed by shampooing (Suave, Daily Clarifying Shampoo, Unilever). Then rinse, squeeze, air dry and comb.

Step 7: Immerse in "hot" (50-55° C.) 2% shampoo solution for 30 min. Then rinse, squeeze, air dry and comb.

Due to insolubility in the alcohol:acetone solvent combination employed in most of the experiments included in Table 1, (light) mineral oil (Embodiment 7, Table 1) and petrolatum (Embodiment 9, Table 1) were solubilized for use with sodium lauryl sulfate.

In a series of experiments (Embodiments 15-17, Table 1) saponified oil solutions were employed as the Cross-Linking Composition referred to in Hair Treatment Procedure, Step 3 (above). These were prepared under ambient conditions by dissolving 0.5 g NaOH in 92 g anhydrous ethanol and then adding 7.5 g of oil, while stirring throughout. The resultant mixture was allowed to stand at room temperature for 10-12 hours prior to use in hair treatment. Because alkali was consumed by the saponification reaction, pH was typically lowered to ~9 (as determined after the addition of water). In some cases the resultant mixture proved ineffective in straightening hair because most of the sodium hydroxide was consumed during the saponification reaction. Effectiveness was, however, restored upon the introduction of additional of sodium hydroxide (0.25% or 0.5% of total weight). This demonstrates the need for adequate quantities of alkali to be present to achieve effectiveness.

Measurement of Tress Length:

~2 g bound tresses of human hair (15-20 cm in length) were vertically mounted on a board ensuring that they hung freely. With care to avoid stretching, tress length was measured from the point where the hair emerged from the material bonding the hair strands together (at the portion of the hair closest to the root) to the opposing extremity (hair tip). Dry tresses were measured before and after (upon completion of Step 7 of Hair Treatment Procedure, above) straightening treatment and the ratio of the latter to the former (i.e., length after treatment/length before treatment) was considered a meaningful measure of the effectiveness of the procedure (See Table 1, Straightening Effectiveness Ratio).

It should be noted that tresses treated by each of the described chemical combinations appeared to be completely straightened after flat iron treatment and prior to shampooing but this was a temporary effect and not considered to be significant. Instead, straightness after hot shampooing, (Hair Treatment Procedure, Step 7) was considered the true barometer of treatment effectiveness. Tresses that remained straight after being subjected to cold shampooing (Hair Treatment Procedure, Step 6) exhibited ratios of 1.25-1.30. Correspondingly, tresses that remained straight after hot shampooing exhibited lower ratios in the range of 1.10-1.30. Ratios determined after hot shampoo treatment (Hair Treatment Procedure, Step 7) are reported in Table 1 and are considered to be the most significant indicator of treatment effectiveness and durability.

TABLE 1

Alkali and Oil Based Reshaping of Hair

| A | NaOH Conc (% w/w) | Cross-Linking Agent | Comment | Straightening Effectiveness Ratio (SER) |
|---|---|---|---|---|
| 1 | 0.6 | 8% Soybean Oil | Effective | 1.22 |
| 2 | 0.6 | 8% Coconut Oil | Effective | 1.27 |
| 3 | 0.6 | 8% Olive Oil | Effective | 1.22 |
| 4 | 0.6 | 8% Castor Oil | Less effective | 1.16 |

TABLE 1-continued

Alkali and Oil Based Reshaping of Hair

| A | NaOH Conc (% w/w) | Cross-Linking Agent | Comment | Straightening Effectiveness Ratio (SER) |
|---|---|---|---|---|
| 5 | 0.6 | 8% Flax Seed Oil 8% Safflower Oil | Effective | 1.27 |
| 6 | 0.5 | Oleosome: Hydrasia ™ (Botaneco) | Effective | 1.22 |
| 7 | 0.5 | 8% Mineral Oil | Partially effective | 1.16 |
| 8 | 0.5 | 8% Lanolin | Partially effective | 1.16 |
| 9 | 0.5 | 8% Petrolatum | Partially effective | 1.11 |
| 10 | 0.5 | 8% Soybean Oil then 0.1N $H_2SO_4$ | Ineffective, Alkali neutralized | 1.06 |
| 11 | 0.5 | 3% Olive Oil (Alcohol) | Effective | 1.22 |
| 12 | 0.5 | 10% Olive Oil (Alcohol) | Effective | 1.26 |
| 13 | 0.5 | 8% Coconut Oil | Effective | 1.30 |
| 14 | 0.5 | 8% Oleic Acid | Ineffective, alkali neutralized | 1.09 |
| 15 | 0.5 | Saponified Olive oil | Ineffective, alkali neutralized, as Item 14 | 1.04 |
| 16 | 0.5 | Saponified Soybean oil | Ineffective prior to the addition of 0.25% NaOH (w/w based on weight of saponified oil solution), whereupon became partially effective. | 1.13 |
| 17 | 0.5 | Saponified Soybean oil | Ineffective prior to the addition of 0.5% NaOH (w/w based on weight of saponified oil solution), whereupon became effective. | 1.22 |

A = Embodiment Number

Process Variables

The most important variables impacting straightening are considered to be the nature and concentration of the alkali as well as the duration of the alkali treatment; the nature of the oil; the force with which the hair is stretched to straightness; and the temperature as well as the duration of the flat iron process. Related to selection of oil, it has been found that vegetable oils are much more effective than mineral oil. This is attributed to the latter having difficulty in penetrating the hair. See, for example, "Secondary Ion Mass Spectrometric Investigation of Penetration of Coconut and Mineral Oils into Human Hair Fibers: Relevance to Hair Damage", S. B. Ruetsch, Y. K. Kamath, Aarti S. Rele, and R. B. Mohile, J. Cosmet. Sci., 52, 169-184 (2001), incorporated by reference herein.

The effect on straightening of the temperature to which the flat iron is heated was investigated in a number of experiments. Tresses were treated with a composition of 0.5% sodium hydroxide and soybean oil. Temperature was varied between 120 and 180° C. with the surface temperature of the flat iron being determined by an infrared thermometer (Infrared Laser Surface Thermometer, measurement range 50-550° C., Maverick Industries, Inc. Edison, N.J. 08837) prior to contact with a tress. After a post treatment hot shampoo, the tress treated at 180° C. was distinctly straighter (SER 1.22) than the tress treated at 150° C. (SER 1.11), which was distinctly straighter than the tress treated at 120° C. (SER 1.02). These results were considered in selecting 180-200° C. flat iron temperature for most of the testing reported herein.

The effect on straightening of the time during which tresses are exposed to the flat iron at 180° C. was also tested. The time was varied from 40-120 seconds. Under the test conditions, 40 seconds proved to be inadequate, while greater than 80 seconds provided no additional benefit. These results were considered in selecting 60-90 seconds for use in most of this work.

In addition to impacting efficacy of straightening, temperature and duration of flat iron treatment significantly impacts the condition and integrity of post-treatment hair. If these variables are not properly controlled hair damage can result. In this regard, it is important to treat thin sections of hair strands during each pass of the flat iron to ensure efficient heat transfer and consequentially, rapid and effective straightening. When properly executed, the molecular processes which alter the structure of hair take place quickly with minimum damage to hair.

Related to the hot shampoo treatment employed to predict the effectiveness of the straightening procedure, it should be noted that during early experiments tresses were treated at 50-55° C. for 1 h but it was subsequently realized that valid results could be gained in 0.5 h. Further, it was noticed that the configurational changes occur in the fiber as soon as the tress contacts the hot shampoo solution, and it remains in that condition as long as the temperature remains unchanged. Molecular movements occur very quickly due to a combination of higher temperature and swelling. Subsequent changes are very slow. Therefore, 30 minutes of hot shampoo treatment was used for most of the work to simulate washing of hair 6-7 times.

Possible Reaction Mechanism

Functionality of the lye based relaxers primarily employed for dense, curly hair is generally attributed to lanthionization in the bulk of hair. In the lye based relaxer process, the hydroxyl ion reacts with cystine to form dehydroalanine which then reacts with cysteine to form lanthionine. During such treatment disulfide bonds are broken in locations that are stressed when the hair fiber is placed in a straightened configuration and lanthionine cross-links are formed to stabilize this revised arrangement. This reaction is known to occur at room temperature and the thioether (lanthionine) linkage thus formed is known to be more stable than the disulfide bond. The effectiveness of the relaxer is greatly dependent on the relatively high concentration of the lye and the resultant softening of the fiber allowing the hair to gently be stretched to straightness. It is important to note that the relatively high concentrations of lye employed in these products inflicts significant damage to hair and poses a hazard to skin and eyes during use. Heat generating flat irons, or similar, cannot be used in this process, because they would exacerbate the damaging effects of the lye to the point of causing massive hair damage and breakage and significantly increase the potential for such formulations to damage the skin and eyes.

When employed at ambient temperatures, 0.5% sodium hydroxide is not of adequately high concentration to soften the hair and form sufficient thioether cross-linkages to stabilize it in a revised configuration. Correspondingly, the potential for lye to damage the hair, skin and eyes is significantly decreased at this concentration as compared with 2.0-2.5% sodium hydroxide typically employed in lye relaxers. 0.5% sodium hydroxide alone cannot durably straighten hair even when employed in conjunction with a flat iron heated to 180-200° C. In surprising contrast, however, durable straightening is achieved by sodium hydroxide under the same conditions in the presence of oil. This suggests a different reaction mechanism is undergone in the presence of oil and one in which the oil is an active participant.

In an experiment, two tresses with distinct natural curl were treated with 0.5% sodium hydroxide for 30 min. (the time was extended to ensure diffusion of sufficient sodium hydroxide into the hair) and, for one of the tresses only, this was followed by treatment with soybean oil for 30 min. After squeezing excess liquid from both tresses they were treated with 0.1N sulfuric acid to neutralize the alkali and were then subjected to flat iron treatment for 90 seconds. Both tresses appeared as straight at that point but turned curly on cold shampooing, and even more curly on hot shampooing. Noting that the comparable procedure resulted in durable straightening for the soybean oil treated tress when the acid neutralization step was omitted (Embodiment 1, Table 1), this suggests that at the high temperature of the flat iron a reaction occurs between the alkali, oil and the keratin protein of hair to stabilize the straightened structure of hair. One possibility is that the oil is hydrolyzed to fatty acids which react covalently with the protein to form hydrophobic bonds (secondary valence) that stabilize the new structure. Also, at these high temperatures, other covalent cross-links can form by dehydration between the proteins molecules in the matrix.

Alternative Reverse Embodiments

In the above embodiments, straightening with sodium hydroxide and oil is achieved in a process that uses two consecutive application steps wherein hair was first treated with sodium hydroxide composition and then with an oil composition. In alternative embodiments, the application of the compositions is reversed, such that the oil composition is applied to the hair first, followed by the sodium hydroxide solution, followed by heat treatment as in the above embodiments.

Alternative One-Step Embodiments

In the above embodiments, straightening with sodium hydroxide and oil is achieved in a process that uses two consecutive application steps wherein hair is treated separately with sodium hydroxide and oil solutions. Alternative embodiments have been developed in which the sodium hydroxide and oil-containing compositions are combined and applied to the hair in a single step.

Because the primary functional components, sodium hydroxide and oil, chemically react if allowed to remain in mutual contact they are combined immediately prior to use. Oil-containing compositions alternative to solvent solutions were employed in this one-step process but are suitable for use in both one- and two-step application procedures, including the two-step embodiments set forth above. Those alternative oil-containing compositions developed to this point vary in form from gels to emulsions but may take any of the forms and consistencies known to the art for containing or delivering oil, including, for example, oleosomes. Similarly, sodium hydroxide has been employed in solution in the work described herein, but may be contained in any form or composition known to the art for containing or delivering this or similar inorganic alkaline ingredients, most notably that of a gel or emulsion. A representative oil-containing composition in the form of a simple emulsion thickened with an inorganic rheology modifier is described in Table 2A below:

TABLE 2A

Example of a simple emulsion system containing oil (% w/w):

| Component | Percentage (w/w) |
|---|---|
| Olive Oil (extra virgin) | 10.11 |
| Tween 20 | 1.52 |
| Cetearyl Alcohol | 0.75 |
| Laponite gel (e.g., Reo-Gel 7.5% XLG, Resonant Technology, Pilesgrove, NJ) | 20.22 |
| Water | 67.40 |
| Total | 100.00 |

A more general formulation of an oil-containing composition of the present invention is described in Table 2B below:

TABLE 2B

General formulation of emulsion systems containing oil (% w/w):

| | INGREDIENT-TRADE NAME | SOURCE | INGREDIENT - INCI NAME | CONC. RANGE (% w/w) Broad | CONC. RANGE (% w/w) Pref. | PURPOSE | ALTERNATES |
|---|---|---|---|---|---|---|---|
| 1 | Sodium Hydroxide | General | Sodium Hydroxide | 0.5-2.5 | 0.5-1.0 | Alkaline agent to saponify oil (grease/fat/wax); swell hair; disrupt protein bonds; crosslink hair | Potassium hydroxide, Lithium hydroxide, Ammonium hydroxide, Barium hydroxide, Beryllium hydroxide, Calcium hydroxide, Cesium hydroxide, Zinc hydroxide - alone or in combination. Guanidine carbonate and Calcium hydroxide in combination |

TABLE 2B-continued

General formulation of emulsion systems containing oil (% w/w):

| | INGREDIENT-TRADE NAME | SOURCE | INGREDIENT - INCI NAME | CONC. RANGE (% w/w) Broad | Pref. | PURPOSE | ALTERNATES |
|---|---|---|---|---|---|---|---|
| 2 | Tween 20 | Croda (numerous additional) | Polysorbate 20 | 0.5-2.0 | 0.5 1.0 | Solubilization, wetting | Numerous nonionic surfactants from numerous suppliers. |
| 3 | Cetearyl alcohol | Croda (numerous additional) | Crodacol CS-50 | 0.5-1.0 | 0.5-1.0 | Thickening, lubrication slip, conditioning | Cetyl alcohol, Stearyl alcohol, Lauryl Alcohol, and numerous additional fatty alcohols |
| 4 | Laponite gel | Resonant Technology | TBD | 0-22 | 0-5 | Thickening, suspending agent | Numerous thickening and suspending agents/polymers currently employed in hair products (e.g., hydroxyethylcellulose, methylcellulose, acrylates/C10-30 Alkyl Acrylate Crosspolymer [Carbopol], |
| 5 | Olive oil | General | *Olea Europeaea* (Olive) Fruit Oil | 0-12 | 2-5 | Cross-link hair, lubrication, slip, conditioning | All vegetable, seed and petroleum derived oils, greases, fats and waxes. *Hydresia oleosomes* (Botaneco) most notably Hydresia SF2; PE and O (*Carthamus Tinctorius* (Safflower) Oleosomes + Water) |

(1) Croda Inc., Edison, NJ
(2) Botaneco, Calgary, Canada
(3) Resonant Technology, Pedricktown, NJ In one embodiment, during the preparation of the composition of Table 2A, all ingredients except cetearyl alcohol were combined under ambient conditions with mechanical stirring (continued throughout preparation). The mixture was heated to 60° C., at which point the cetearyl alcohol was added. After reaching homogeneity the batch was allowed to cool under ambient conditions resulting in a thick emulsion. The sodium hydroxide solution was mixed into the oil-containing emulsion immediately prior to use in hair straightening such that the concentration of sodium hydroxide in the resulting test emulsions ranged from 0.25 to 1.08 percent (w/w).

It is generally desirable for the combined oil and alkaline (e.g., sodium hydroxide) compositions to be sufficiently thick so as not to run from the hair during application but it is not necessary for either or both of the compositions to be thick prior to mixing. Related technologies employed in permanent hair dye formulation can be utilized for this approach (as in the case of permanent hair dyes a highly alkaline composition is typically mixed with a non-alkaline composition and the resultant composition is significantly alkaline). For example a water insoluble fatty alcohol (e.g., cetyl alcohol, lauryl alcohol) may be solubilized in either the aqueous oil or aqueous alkali composition. Upon combination with the second aqueous composition, a portion of the effectiveness of this solubilization is lost due to the introduction of additional water and as a consequence thickening occurs. Another approach is to include an alkali-swellable polymer such as Acrylates/Steareth-20 Itaconate Copolymer (for example, Structure® 2001, AkzoNobel Global Personal Care) in the aqueous oil formulation. Thickening occurs when this formulation is combined with the sodium hydroxide composition due to resultant highly alkaline pH.

Hair Treatments

A single tress (~3 g, ~20 cm in length) was treated with the olive oil-containing emulsion described in Table 2 (combined with sodium hydroxide solution prior to application) and a comparable tress was treated with a Control composition in which the formula weight of olive oil was replaced by additional water with all other ingredients remained unchanged. The assigned emulsion (combined with sodium hydroxide solution prior to application) was massaged into each tress (~20 g per tress) with a spatula while continuously stretching and straightening the hair during the process (tension was continuously applied by spatula while distributing the product directionally from the root end towards the tip of the hair). After 20 min. the tresses were squeezed between the index finger and thumb and combed to remove excess emulsion. The tresses were then treated with a flat iron at 180-200° C. for 90 seconds and, after cooling, were shampooed in cold water. After removing excess water by squeezing and combing, the tresses were air dried and measured for length. The tresses were then dipped in a hot shampoo bath for 0.5 hours and rinsed. After excess water was removed as above, the tresses were air dried and measured for length.

The amount of sodium hydroxide removed from each emulsion by the hair, both through physical absorption and chemical reaction, was determined from the sodium hydroxide content of the residual emulsions. (Loss of sodium hydroxide due to chemical reaction with the oil was not considered because this was not expected to be significant under the conditions of treatment, i.e., room temperature for approximately 20 minutes.) For this purpose, aliquots of the Test and Control emulsions, both before and after their use in hair treatment, were titrated with 0.25N sulfuric acid using phenolphthalein indicator. The calculations employed to determine sodium hydroxide content before and after tress treatment, and therefore, the amount removed by each tress are provided in Table 3 and results of this study are provided in Table 4.

TABLE 3

Calculations - Determination of sodium hydroxide removed from emulsions by hair

Prior to Straightening Treatment:

| | |
|---|---|
| $Y_1$ = g NaOH in emulsion/g of emulsion = | 0.01 X*/g emulsion |

After Straightening Treatment:

| | |
|---|---|
| $Y_2$ = g NaOH in emulsion/g of emulsion = | 0.01 X*/g emulsion |
| W = g NaOH removed from emulsion by tress = | $(Y_1 - Y_2)$(g emulsion used in treatment) |
| W/g hair in tress = | g. NaOH removed from emulsion by tress/g hair in tress |

*X = ml 0.25N $H_2SO_4$ required to titrate NaOH

TABLE 4

Sodium hydroxide removed by hair from oil-, and non oil-containing emulsions as a function of sodium hydroxide concentration

| NaOH Conc. in Emulsion (% w/w) | NaOH Removed from Control (Non Oil) Emulsion (g NaOH/g Hair) | NaOH Removed from Test (Olive Oil) Emulsion (g NaOH/g Hair) |
|---|---|---|
| 0.25 | 0.0044 | 0.0072 |
| 0.50 | 0.0118 | 0.0160 |
| 0.85 | 0.0130 | 0.0190 |
| 1.08 | 0.0160 | 0.0200 |

Table 4 shows that for each concentration level of sodium hydroxide tested, a larger amount of sodium hydroxide was removed by hair from the olive oil-containing (Test) emulsion than from the non oil-containing (Control) emulsion. Increase of sodium hydroxide concentration from 0.25 to 0.5% resulted in greater than 100% increase in amount of sodium hydroxide removed by tresses from both the Test and Control emulsions, however further increases had markedly reduced effect. These findings strongly suggest this effect to result from the repulsive potential of a negatively charged double layer of hydroxyl ions formed at the surface of hair. At low sodium hydroxide concentrations the repulsive potential is low and therefore the negatively charged hydroxyl ions can easily diffuse into the hair. At higher concentrations the repulsive potential increases and repels the hydroxyl ions, thus restricting access into the fiber. The effectiveness of these formulations in straightening hair is provided in Table 5.

TABLE 5

Straightening performance of emulsions as a function of sodium hydroxid concentration

| | Straightening Effectiveness Ratio (SER) | | | |
|---|---|---|---|---|
| NaOH Conc. in | Control (Non-Oil) Emulsion | | Test (Olive Oil) Emulsion | |
| Emulsion (% w/w) | Cold Shampoo | Hot Shampoo | Cold Shampoo | Hot Shampoo |
| 0.25 | 1.08 | 1.06 | 1.08 | 1.04 |
| 0.50 | 1.18 | 1.06 | 1.24 | 1.18 |
| 0.85 | 1.18 | 1.10 | 1.20 | 1.12 |
| 1.08 | 1.22 | 1.08 | 1.22 | 1.16 |

Based on results after hot shampoo, the Straightening Effectiveness Ratios (SER) presented in Table 5 show that the most effective straightening within this series (SER of 1.24) is achieved at 0.5% sodium hydroxide in the presence of olive oil. Again, it is noted that results after hot shampoo were assigned prime importance because of the stringency by which this procedure challenges the effectiveness and durability of straightening performance. These finding are contrary to the expectations based on the prior art wherein increased sodium hydroxide concentration would have been expected to be the overwhelming driver of straightening performance.

Thus, novel methods and chemical compositions for reshaping hair have been presented. Although the invention has been described using specific example embodiments, substances, and method steps, those of ordinary skill in the art will understand that the invention is not limited to the specific example embodiments described herein. For example, the various solutions used in may contain other ingredients (such as proteins, for example) in addition to or instead of the ones described in the example embodiments, and the method may contain one or more steps in addition to or instead of the specific steps described in the example embodiments. Other embodiments will be apparent to those skilled in the art.

The invention claimed is:

1. A method for straightening hair comprising the steps of:
   obtaining a first composition comprising between about 2 and 12 percent by weight of an oil and about 67 percent by weight of water;
   creating a second composition by adding a component comprising alkaline hydroxide to said first composition such that the concentration of said alkaline hydroxide in said second composition comprises between about 0.25 and 1.08 per cent by weight;
   applying said second composition to said hair immediately after creating said second composition;
   removing an excess of said second composition not absorbed by said hair after passage of a first period of time;
   applying straightening tension to said hair while applying heat at a temperature of between about 180 and 200 degrees centigrade.

2. The method of claim 1 wherein said first period of time is about 20 minutes.

3. The method of claim 1 wherein said oil comprises a vegetable oil.

4. The method of claim 1 wherein said alkaline hydroxide comprises sodium hydroxide.

5. The method of claim 1 wherein said heat is applied to said hair at a temperature less than 190 degrees centigrade.

6. The method of claim 5 wherein said heat is applied with a hair straightening iron.

7. The method of claim 1 wherein said first composition comprises about 10 percent by weight of said oil.

8. The method of claim 1 wherein said first composition comprises an emulsion.

9. The method of claim 1 wherein said first composition comprises an a gel.

10. The method of claim 1 wherein said first composition comprises an oleosome.

11. The method of claim 1 wherein said component comprising said alkaline hydroxide comprises a solution.

12. The method of claim 1 wherein said component comprising said alkaline hydroxide comprises a gel.

13. The method of claim 1 wherein said first composition comprises a rheology modifier.

14. The method of claim 13 wherein said first composition comprises about 20 percent by weight of said rheology modifier.

15. The method of claim 14 wherein said rheology modifier comprises a Laponite gel.

16. The method of claim 1 wherein said first composition comprises about 0.75 percent by weight of an alcohol.

17. The method of claim 7 wherein said first composition comprises about 20 percent by weight of an inorganic rheology modifier.

18. The method of claim 17 wherein said first composition comprises about 0.75 percent by weight of an alcohol.

* * * * *